US005688682A

United States Patent [19]

Mulks et al.

[11] Patent Number: 5,688,682
[45] Date of Patent: Nov. 18, 1997

[54] METHOD FOR PRODUCING A BACTERIAL VACCINE AND NOVEL VACCINES PRODUCED THEREBY

[75] Inventors: Martha H. Mulks, Williamston; Brad J. Thacker, Bath, both of Mich.

[73] Assignee: Board of Trustees operating Michigan State University, East Lansing, Mich.

[21] Appl. No.: 601,835

[22] Filed: Feb. 15, 1996

Related U.S. Application Data

[63] Continuation of Ser. No. 107,856, filed as PCT/US93/03848 Apr. 23, 1993, abandoned.

[51] Int. Cl.$^6$ .............................. C12N 1/12; C12N 1/00; G01N 33/531; A61K 39/01
[52] U.S. Cl. ............................ 435/252.1; 435/173.4; 435/173.7; 435/243; 435/961; 425/825; 425/256.1; 425/234.1; 514/54
[58] Field of Search ................... 424/256.1, 825, 424/234.1; 435/173.4, 173.7, 252.1, 961, 243; 514/54

[56] References Cited

U.S. PATENT DOCUMENTS

| 3,862,313 | 1/1975 | Fryer et al. | |
|---|---|---|---|
| 4,070,454 | 1/1978 | Relyveld | |
| 4,157,390 | 6/1979 | Purry et al. | 424/92 |
| 4,298,597 | 11/1981 | Acres et al. | |
| 4,707,543 | 11/1987 | Zollinger et al. | |
| 4,837,018 | 6/1989 | Konishi et al. | 424/92 |
| 5,332,572 | 7/1994 | Ross et al. | 424/234.1 |

FOREIGN PATENT DOCUMENTS 453024  10/1991  European Pat. Off.

OTHER PUBLICATIONS

Nielsen R. Nord. Vet. Med. 36:221–234, 1984.
Fenwick et al, Infect. Immun 54(2): 575–582, 1986.
Deutscher M, Methods in Enzymology 182:83–89, 1990.
Linn S, Methods in Enzymology 182: 9–15, 1990.
Austrian, R., Bacterial Vaccines, Academic Press, Inc. "Pneumococcal Infections", Chapter 9, 257–285 (1984).
Mulks, Martha, et al., Proc. Int. Pig Veter. Soc. 10 81 (1988).
Alliger, Ultrasonic Disruption, reprinted from American Laboratory, 7 pages (1975).
Davis et al, Microbiology, 3rd Ed. Harper & Row, New York, pp. 7, 447–448 (1980).
Rawn, J. David, Biochemistry, Harper & Row, pp. 164, 564 (1983).
Fedorka–Cray et al., Abstracts of the Annual Meeting—ASM Abst #B-37 (1988).
Bhatia, B., Veterinary Microbiology, 29, 147–158 (1991).

*Primary Examiner*—N. M. Minnifield
*Attorney, Agent, or Firm*—Ian C. McLeod

[57] ABSTRACT

A new method for the preparation of a whole cell bacterial vaccine for improved protection against bacterial pathogens, particularly against those pathogens which have multiple antigenic serotypes is described. The method particularly involves selective sonication of the whole cells of virulent strains of the bacteria. The preferred vaccine prevented infection of swine with *Actinobacillus pleuropneumoniae* (APP), which causes porcine contagious pleuropneumonia. The vaccine has good safety and few side effects even at a higher dose than commonly used for bacterins and improved protection against the homologous serotype of the pathogen; and improved cross-protection against heterologous serotypes. The whole cell vaccine, is most useful for veterinary (lower mammal) vaccines.

12 Claims, No Drawings

METHOD FOR PRODUCING A BACTERIAL VACCINE AND NOVEL VACCINES PRODUCED THEREBY

This application is a continuation of application Ser. No. 08/107,856 filed on Sep. 14, 1993 now abandoned, which is a national application based upon PCT/US93/03848, filed Apr. 23, 1993, which PCT application claims benefit of U.S. application Ser. No. 874,101, filed Apr. 27, 1992 now abandoned.

BACKGROUND OF THE INVENTION

(1) Field of the Invention

The present invention relates to a method for producing a vaccine from a pathogenic bacterium. In particular, the present invention provides a method for producing a whole cell derived vaccine which has a broad spectrum of activity in producing immunity in a host against multiple serotypes of the bacterium, particularly in pigs.

(2) Prior Art

Most prior art bacterial vaccines are based upon killing a virulent strain of the bacteria by using formalin or by heat killing the bacteria. Generally the bacterial cells are a single serotype of the target bacteria. As a result, heterologous serotypes of the same bacteria can cause disease in spite of vaccination. The reason for this is not completely understood; however, it appears that antibodies to the heterologous serotype are not induced by the vaccine and thus there is no immunity.

Sonicating bacteria is also described by U.S. Pat. Nos. 3,862,313 to Fryer et al, 4,298,597 to Acres et al and U.S. Pat. No. 4,707,543 to Zollinger et al. In Fryer et al, the bacterial cells are formalin killed prior to sonication. Formalin treatment may alter bacterial components, making them less antigenic. Acres et al describe a vaccine prepared using multiple strains to produce the vaccine which is active against heterologous serotypes of the bacteria. The vaccine also contains cell fragments resulting from sonication or mechanical shearing. Zollinger et al describe an outer membrane complex which is isolated from the bacterium. The vaccines of the prior art have limited effectiveness against heterologous serotypes of a particular bacterium for which immunity is required.

Outer membranes (OM) have been used to produce vaccines. Proc. Int. Pig Veter. Soc. 10 81 (1988) by the present inventors describes an OM vaccine for pigs derived from *Haemophilus pleuropneumoniae* (now known as *Actinobacillus pleuropneumoniae*). The vaccine contained APP outer membranes. Such vaccines are effective. The OM were produced by sonication of lysozyme-sucrose treated cells and then sucrose density gradient centrifugation. The sonication was for 10–15 seconds. Lysozyme degrades peptidoglycan (cell wall). Sucrose maintains the cell membranes remaining after treatment with the lysozyme until the cells are sonicated. No preservative was used in the preparation of the vaccine. Sucrose density gradient centrifugation and separation of OM is not a commercially viable method for producing the vaccine.

There is a need for an improved method for commercially producing bacterial vaccines, particularly those effective against porcine contagious pleuropneumonia, caused by *Actinobacillus pleuropneumoniae*.

OBJECTS

It is therefore an object of the present invention to provide novel vaccines produced by a method which is commercially viable where the vaccine provides immunity to homologous and heterologous serotypes of a bacterium. Further, it is an object of the present invention to provide a method which is relatively easy to perform, safe and reliable. These and other objects will become increasingly apparent by reference to the following description.

GENERAL DESCRIPTION

The present invention relates to a method for producing a vaccine from cells of a pathogenic bacterium which produces a disease in a host which comprises: isolating a strain of the bacterium from the host in a virulent form by passage of the strains through the host; growing the isolated strain in a growth medium; harvesting the strain from the growth medium; disrupting the cells of the strain in an aqueous solution for a short period of time to expose capsular and subcapsular antigenic materials; and preserving the antigenic materials in the aqueous solution with a preservative agent which kills the bacterium to provide the vaccine wherein the vaccine provides immunity to the disease when injected into the host.

The present invention relates to a method for producing a vaccine from a pathogenic bacterium which produces a disease in a host which comprises: isolating a strain of the bacterium from the host in a virulent form by passage of the strains through the host; growing the isolated strain in a growth medium; harvesting the strain from the growth medium; sonicating the strain in an aqueous solution for a short period of time to expose capsular and subcapsular antigenic materials; and preserving the antigenic materials in the aqueous solution with a preservative agent which kills the bacterium, preferably without impairing the antigenic materials, to provide the vaccine, wherein the vaccine provides immunity to the disease when injected into the host. It was particularly unobvious to one skilled in the art that sonicated whole cells could provide a useful vaccine, since disrupted cells contain so many cellular components, and that purification of the outer membrane was unnecessary. It was further unobvious that cross-reactivity against various strains of APP could be achieved using this method. The invention also relates to vaccines prepared by this method, particularly vaccines containing hemolysin enhanced supernatant.

It is preferred to use a hemolysin enriched supernatant (HES) which is produced by APP. The HES contains hemolysin and cytotoxins (Hly/Cly) produced by APP, which are high molecular weight extra-cellular protein toxins. These include Hly/Cly I which is 105 Kd; Hly/Cly II which is 103 Kd and Cly III which is 120 Kd. There are most likely other toxins produced. These proteins kill host red and/or white blood cells. HES is desirable for use in the vaccines of the present invention to insure broad immunity, but is not necessary.

In the present invention, the following factors are important in producing a commercially useful vaccine:

1. The selection of bacterial strains. Through several years of experience working with bacteria, particularly *Actinobacillus pleuropneumoniae* (APP), it has been learned that it is very important to use carefully selected strains as freshly isolated from the host animal as possible. Virulence and thus expression of factors necessary for virulence which should be included in any vaccine as important antigens, can be increased up to 1,000–10,000 fold in this manner.

2. The media and growth conditions. Media and growth conditions are selected which optimize the production of important virulence factors of this bacterium, including capsular polysaccharide, hemolysins, and common outer membrane proteins.

3. The choice of conditions for production of sonicated cells.

4. The choice of adjuvant and vaccination schedule.

5. The choice of vaccine preservative. The most commonly used preservative, formalin, reduced the efficacy of the vaccine against heterologous serotypes of APP.

6. The maximum safe dosage. A safety trial was conducted with APP vaccine comparing different dosages for both safety and efficacy in inducing an immune response.

7. Safety and immunogenicity in the field. A field trial was conducted to test the efficacy of APP vaccine in a swine herd with a chronic problem with APP and judged to be effective.

The new method for the preparation of bacterial vaccines is designed to produce a vaccine that provides improved protection against bacterial pathogens, particularly against those pathogens which have multiple antigenic serotypes. Because the product is a modified whole cell vaccine, this procedure is most useful for veterinary rather than human vaccines wherein whole cell vaccines may be perceived as too risky.

The particular pathogen-host system that was utilized in the development of the method of the present invention is *Actinobacillus pleuropneumoniae* infection in swine. This is a representative gram-negative bacterial pathogen that causes pleuropneumonia. There are at least twelve (12) different antigenic serotypes of this organism. Current commercial vaccines are generally formalinized or heat killed whole cell bacterins. These bacterins provide moderate protection against infection with the homologous serotype, that is, the serotype used to produce the vaccine, but minimal protection against heterologous serotypes. In contrast, infection with the live organism generally elicits an immune response that protects against subsequent infection with any serotype. These data suggested that there are common antigens shared among the serotypes that might elicit cross-protective immunity, but that these antigens are not well exposed in whole cell bacterin vaccines. The method of the present invention enhances exposure of these antigens, which in APP are subcapsular outer membrane proteins and lipopolysaccharides and hidden capsular antigens, to produce a more effective, cross-protective vaccine.

An important component of this procedure is disruption of the bacterial cells prior to the addition of any preservative in a manner which enhances the exposure of important subcapsular antigens. The methods are well known and include sonication or the use of a French press which disrupts the cells by a sudden reduction of pressure on a fluid. Once bacterial cultures have been grown and harvested, cells are sonicated to rupture the cells and enhance exposure of outer membrane antigens. After sonication, preservatives, such as sodium azide, are added.

It is important to use either fresh clinical isolates or type strains that have been freshly passaged through a host animal to regenerate production of virulence factors. All strains used should be isolated from infected animal tissues and frozen at −70° C. or lyophilized immediately. For production of vaccine, bacteria should be plated from the storage vial and used immediately for vaccine production, with no subsequent subculture.

The conditions for sonicating the cells are important. Preferably the sonication is between about 30 and 90 seconds at about 20 KHz output. The duty cycle is preferably 30 (percent of time of sonication) and the output is preferably 40 (percent of maximum amplification). A suitable instrument is a Branson Model 250 Sonifier (Dansbury, Conn.). This enables the exposure of the capsular and subcapsular antigenic materials without destroying them. Sonication for too long a time reduces the antigenic character of the vaccine. Usually sonication for less than two (2) minutes is sufficient.

The media for growth depends upon the bacterium being used and is selected to provide maximum virulence. Bergey's Manual of Determinative Bacteriology (8th Edition 1974) or later editions describe media for bacteria. The bacteria which are disease producing and thus suitable for vaccine production are also described.

The preservative agent which is preferred is sodium azide. This compound blocks electron transport within the membrane of the cells so that there is no generation of energy for the cells and thus the cells die. The compound is a "metabolic poison" which does not tan the proteins. Other useful preservative agent compounds are beta propiolactone, thimerosal, and binary ethyleneimine. The compounds assure that the cells are non-living. Preservatives that are metabolic inhibitors rather than fixatives are preferably used.

The preferred adjuvant for the vaccine was Emulsigen™ (MVP Labs, Ralston, Nebr.), which is a paraffin oil in water emulsion, since it can be used in food animals. Freunds Incomplete Adjuvant. which is 15 percent by weight mannide monooleate and 85% paraffin oil, available from Difco, Detroit, Mich. can be used in non-food (i.e. laboratory animals). The adjuvants aid in slowly releasing the vaccine into the animal and in potentiating the immune response. Any commercial oil emulsion adjuvants can be used but not aluminum hydroxide.

SPECIFIC DESCRIPTION

In the model system used to develop the vaccine against APP infection in swine, there are multiple serotypes of the infecting organism, with serotypes based on antigenic differences in the capsular polysaccharides. Infection with one serotype provides protection against subsequent challenge with all serotypes. However, formalinized or heat-killed bacterins provide moderate protection against the homologous serotype and essentially no protection against heterologous serotypes. Research on antigens of APP and the immune response of swine to those antigens showed that there are a variety of antigenically similar outer membrane proteins that are found in all isolates of APP, regardless of serotype, which contribute to cross-protective immunity. The outer membrane (OM) vaccine, produced by the inventors herein, but not by others, provided complete protection against both homologous and heterologous serotypes of APP in swine. The procedure for the preparation of the vaccine, however, was too labor and equipment intensive, and thus too expensive, for commercial use. The present method is based upon the premise that limited sonication of the bacterial cells exposes common subcapsular surface antigens capable of eliciting a cross-protective immune response. The method is inexpensive to perform and easily adapted to commercial vaccine production.

For optimal vaccine production, media and growth conditions were examined to determine the conditions that optimize expression of important bacterial antigens and virulence factors. In *A. pleuropneumoniae* important antigens include capsular polysaccharide, hemolysin, outer membrane proteins, and lipopolysaccharide. Media and growth conditions and growth stage were chosen to enhance production of hemolysin while maintaining production of other factors, such as capsular polysaccharide.

Use of formalin or similar preservatives that "tan" the bacterial cell surface and that denature protein antigens appears to decrease the efficacy of the vaccine, particularly affecting cross-protective efficacy. Several preservatives were tested and sodium azide was judged to be preferable to formalin (or B-propiolactone) which is also used. Adjuvants that contain formalin also may decrease efficacy.

Example 1

The following is a detailed description of the production of a sonicated whole cell (SWC) vaccine against *Actinobacillus pleuropneumoniae*:

1. Two BHIV (brain heart infusion plus 10 ug/ml NAD—nicotinamide-adenine-dinucleotide) agar plates were inoculated with APP I-178 (a strain maintained at Michigan State University, East Lansing, Mich., and freely available upon request), from a freezer vial of culture which had been reisolated from swine, was grown overnight at 37° C., under 5% $CO_2$.

2. The overnight plate culture was used to inoculate HIV+Ca (heart infusion broth plus 10 ug/ml NAD plus 5 mM $CaCl_2$) broth cultures. 10 ml of broth was inoculated for each vaccine dose planned.

3. Broth culture was grown at 37° C. with shaking at 150–200 rpm, to $OD_{520}=0.8$ (mid- to late-exponential phase). Optical density reflects the number of cells as determined spectrophotometrically using light at 520 nm.

4. Bacterial cells were harvested by centrifugation; the pellets were pooled and the cells were washed once with a buffer which was: 0.01M Tris-acetate, pH 7.5; plus 0.2 mM DTT (Dithiothreitol; DTT is a reducing agent which keeps proteins from clumping together); plus 5.0 mM EDTA (ethylene diamine tetraacetic acid, (a chelating agent for metal ions); plus 0.1% sodium azide.

5. The cells were resuspended in buffer to 1/20 original culture volume.

6. The cells were sonicated on ice (to prevent denaturing), so as not to leave unbroken cells. The buffer solution and cells were at about 8° to 12° C. The sonicate was checked under a phase microscope for unbroken cells. If necessary, sonication was repeated.

For APP vaccine, the cells were sonicated at an output of 40 (level 1–100 power) and a % work (percent of time for working bursts) of 30, for a total time of 60–75 seconds as discussed above.

7. Fresh sodium azide was added to 0.2% final concentration, then the sonicate was held for 24 hours at 4° C. A sample was plated on BHIV agar to check for sterility.

8. The preparation was aliquoted into vaccine doses: 0.5 ml sonicated whole cell (SWC) suspension plus 1.0 ml sterile saline plus 0.5 ml Emulsigen™ adjuvant (MVP Labs, Ralston, Nebr.). The vaccine was held at 4° C. until needed. Table 1 shows the effectiveness of the SWC vaccine as compared to an outer membrane (OM) vaccine and a commercial vaccine.

TABLE 1

| | Saline | HES | OM | OMP + HES | SWC | SWC + HES | Commercial bacterin vaccine |
|---|---|---|---|---|---|---|---|
| Mortality | 6/6 | 0/6 | 0/5 | 0/6 | 0/5 | 0/3 | 3/6 |
| % Pneumonia | 67.2 | 2.7 | 3.8 | 5.7 | 0.2 | 0 | 42.8 |
| % Pleuritis | 81.7 | 1.7 | 4.7 | 4.6 | 0 | 0 | 41.2 |
| Clinical Signs[a] | | | | | | | |
| Temp (Normal = 102.6) | 103.8 | 103.4 | 102.7 | 102.4 | 102.8 | 103.6 | 104.4 |
| Resp. rate (Normal ~ 8 per 75 seconds) | 20.2 | 10.2 | 12.2 | 9.8 | 9.2 | 10.3 | 12.6 |
| Depression (Normal = 0), scale = 0–3 | 2.3 | 0.2 | 0.2 | 0 | 0 | 0 | 1.5 |
| Appetite (Normal = 1, scale = 0–1 | 0 | 1 | 0.8 | 1 | 1 | 1 | 0 |
| 4 wk ELISA titers[b] (antibody response) | 120 | 960 | 7680 | 7680 | 3840 | 3840 | 3840 |
| Weight gain during vaccination period: (kg) | 25.3 | 25.6 | 24.5 | 24.9 | 24.6 | 24.4 | 24.5 |

Dosages:
HES = 2 mg/dose
OM = 5 mg OM/dose
SWC = 1 × $10^{10}$ cfu/dose
[a]12 hours post-infection
[b]antibody titers were measured by ELISA against APP outer membranes. Titer is expressed as the reciprocal of serum dilution.
SWC = Sonicated whole cells
OM = Outer membrane vaccine
HES = hemolysin-enriched supernatant = preparation which is a ultrafiltration concentrated (1:10) supernatant from APP broth culture.
Saline = Saline solution and adjuvant (Emulsigen ™)

Preparation of hemolysin-enriched supernatant (HES):

1. One BHIV plate inoculated with APP I-178, from a freezer vial of culture which had been reisolated from swine, was grown overnight at 37° C. under 5% $CO_2$.

2. The overnight plate culture was used to inoculate 500 ml of heart infusion broth which had been filtered through a 10,000 molecular weight cut-off Amicon membrane prior to autoclaving (filter retentate containing any material with a molecular weight larger than 10,000 was discarded). NAD (10 µg/ml) and $CaCl_2$ (5 mM) were added to the HI broth prior to inoculation.

3. The broth culture was grown at 37° C. with shaking at 150–200 rpm to an $OD_{520}=0.8$ (the point at which peak levels of hemolysin are reached in the culture supernatant).

4. Bacterial cells were pelleted by centrifugation, and the culture supernatant collected.

5. The culture supernatant was concentrated by positive-pressure ultrafiltration through a 50,000 MW cut-off membrane from 500 ml to 25 ml. This process concentrates all materials with a molecular weight of 50,000 or greater, and removes most of the lower molecular weight material. Ultrapure glycerol was added to a final concentration of 20%, and the preparation stored at −70° C. until use.

6. The HES preparation was composed of ~50% high molecular weight (100–120 Kd) hemolysins and 50% outer membrane proteins.

The antibody titers were higher for OM; however, the separation step required for this vaccine makes the production cost prohibitive. The protective efficacy of SWC vaccine was equivalent to OM vaccine.

Example 2

A second APP vaccine prepared as in Example 1 was tested and the results are shown in Table 2.

TABLE 2

|  | Saline | SWC + HES 3 doses | SWC + HES 2 doses |
|---|---|---|---|
| Mortality | 4/5 | 0/5 | 0/6 |
| % Pneumonia | 60.1 | 4.0 | 4.3 |
| % Pleuritis | 21.7 | 1.4 | 4.7 |

The results were as good as those of Example 1.

Example 3

A third APP vaccine prepared as in Example 1 was tested and the results are shown in Table 3

TABLE 3

|  | Saline | SWC + HES (3 doses) |
|---|---|---|
| Mortality | 3/6 | 0/16 |
| % Pneumonia | 53.2 | 1.5% |
| % Pleuritis | 47.5 | 0.4% |

The results were as good as those in Example 1.

Example 4

The purpose of this experiment was to evaluate the safety of and immune response to different dosages of APP serotype 1 and serotype 5 sonicated whole cell vaccines containing hemolysin. The experimental design included 15 groups of 6 pigs each. Each group was vaccinated 3 times at 2 week intervals. The safety of the vaccine was evaluated by measuring temperature and clinical signs after vaccination and the weight gain over the course of the trial as compared to unvaccinated controls. Also the pigs were bled at biweekly intervals to allow evaluation of serum immune responses by ELISA.

For space reasons, each of these 15 groups of 6 were divided into 2 replicate groups of 3 each. The group numbers and dosages are shown in Table 4.

TABLE 4

| Group # | Vaccine Serotype | Vaccine Dosage |
|---|---|---|
| 1 | 1 | 1X ($10^{10}$ cfu/dose) |
| 2 | 1 | 0.5 ($5 \times 10^9$) |
| 3 | 1 | 0.25 ($2.5 \times 10^9$) |
| 4 | 1 | 0.10 ($1 \times 10^9$) |
| 5 | 5 | 1X ($10^{10}$ cfu/dose) |
| 6 | 5 | 0.5 ($5 \times 10^9$) |
| 7 | 5 | 0.25 ($2.5 \times 10^9$) |
| 8 | 5 | 0.10 ($1 \times 10^9$) |
| 9 | 1 & 5 | 1X + 1X ($10^{10} + 10^{10}$ cfu/dose) |
| 10 | 1 & 5 | 0.5 + 0.5 ($5 + 5 \times 10^9$) |
| 11 | 1 & 5 | 0.25 + 0.25 ($2.5 + 2.5 \times 10^9$) |
| 12 | 1 & 5 | 0.1 + 0.1 ($1 + 1 \times 10^9$) |
| 13 | Saline | |
| 14 | Commercial vaccine | |
| 15 | Unvaccinated controls | |

The results are shown in Table 5. It was found that $2 \times 10^{10}$ cfu/dose (half APP-1, half APP-5) can be used with no serious side effects. The weight gains for all 15 groups were similar. Rectal temps (6 and 12 hrs post vaccination) were the same for all APP vaccinates>saline vaccinates>unvaccinated controls. No abscesses or injection site lesions were noted in any group. Since animals were not challenged, no data on vaccine dosage necessary to provide protection was determined.

TABLE 5

| Group | Start Weight | Gain Weight | Week 4 ELISA OD's Serotype 1 | Serotype 5 |
|---|---|---|---|---|
| 1 | 24.0 | 28.5 | 952 | 287 |
| 2 | 23.8 | 30.8 | 824 | 159 |
| 3 | 24.7 | 28.8 | 793 | 167 |
| 4 | 24.2 | 30.5 | 1088 | 272 |
| 5 | 23.1 | 27.3 | 360 | 942 |
| 6 | 24.2 | 29.7 | 205 | 1167 |
| 7 | 23.6 | 29.0 | 195 | 1182 |
| 8 | 24.1 | 30.4 | 147 | 715 |
| 9 | 23.4 | 26.2 | 629 | 661 |
| 10 | 23.6 | 28.3 | 898 | 565 |
| 11 | 24.1 | 26.4 | 1081 | 847 |
| 12 | 24.5 | 29.7 | 1153 | 1026 |
| 13 | 23.9 | 31.2 | 143 | 170 |
| 14 | 23.3 | 31.4 | 643 | 517 |
| 15 | 24.3 | 29.7 | 91 | 86 |

OD = optical density from ELISA
Orders of Values (Descending Order)

| Parameter | Statistical analysis |
|---|---|
| Weight gain | All groups were the same |
| Serotype 1 | 12, 4, 11 1, 10, 2, 3, 14, 9 >>5, 6, |
| ELISA | 7, 8, 13, 15 = two significant groups |
| Serotype 5 | 7, 6, 12, 5, 11, 8, 9, 10, 14 >>1, 4, |
| ELISA | 13, 3, 2, 15 = two significant groups |

Example 5

A field test was conducted comparing a whole cell bacterin, commercial bacterins and the SWC vaccine of Example 1.

Several APP isolates were obtained from a herd with an APP problem (herd LVF). These isolates were serotyped as serotype 1.

Two different autogenous vaccines were prepared: (1) a formalinized whole cell bacterin and (2) a sonicated whole cell SWC vaccine according to the procedure of Example 1. Fifty (50) pigs were vaccinated with each vaccine, two (2) vaccinations at three (3) week intervals, starting when the pigs were 7–8 weeks old. Sera from representative pigs were collected prior to vaccination and 2–3 weeks after the second vaccination, so that the immune responses to these vaccines could be followed. The occurrence of APP in these animals was also monitored. The results are shown in Table 6.

TABLE 6

| VACCINE | ELISA vs APP-1A Pre | Post | ELISA vs APP-LVF Pre | Post |
|---|---|---|---|---|
| Autogenous bacterin (non-sonicated whole cell plus formalin) | | | | |
| Average OD | 125 | 894 | 204 | 1346 |
| Range | 47–238 | 368–1388 | 89–392 | 1058–1634 |
| Autogenous SWC | | | | |
| Average OD | 110 | 842 | 177 | 1357 |
| Range | 47–196 | 453–1462 | 47–371 | 950–1603 |

TABLE 6-continued

| VACCINE | ELISA vs APP-1A | | ELISA vs APP-LVF | |
|---|---|---|---|---|
| | Pre | Post | Pre | Post |
| Commercial Vaccine 1 | | | | |
| Average OD | 105 | 1029 | 159 | 942 |
| Range | 35–242 | 445–1665 | 29–276 | 281–1481 |
| Commercial Vaccine 2 | | | | |
| Average OD | 86 | 740 | 131 | 774 |
| Range | 17–208 | 173–1156 | 39–312 | 206–1275 |

In the ELISA test, uninfected animals from APP-free herds generally give an OD of less than 100. The pre-vaccination titers on some of these animals suggested that they have been exposed to APP, or still have traces of passive immunity acquired from infected or vaccinated sows. The post vaccination responses indicated that the two autogenous vaccines are equivalent. The higher titer against the LVF strain is due to the fact that these were both autogenous vaccines. All the animals tested responded to these two autogenous vaccines with acceptable titers (OD greater than 900). The autogenous bacterin is easier and cheaper to prepare; however, it was found the SWC vaccine leads to better cross-protection against other APP serotypes. Both the autogenous bacterin and the SWC vaccine elicited higher and more consistent antibody responses (ELISA titers) than either commercial vaccine. It was found that the SWC vaccine was as effective as any of the commercial or whole cell bacterins.

The method of the present invention is useful for the production of improved vaccines against any bacterial pathogen. This would include, but not be limited to, all veterinary bacterial pathogens, particularly those where the existence of multiple serotypes is a problem. Equivalent results are obtained with a French press or like system for disruption of the cells without denaturing the peptides or proteins which remain.

It is intended that the foregoing description be only illustrative of the present invention and that the present invention be limited only by the hereinafter appended claims.

We claim:

1. A method for producing a vaccine from cells of *Actinobacillus pleuropneumoniae* for injection into swine to produce immunity which comprises:

(a) isolating a strain of the *Actinobacillus pleuropneumoniae* from a swine infected with the strain in a virulent form as a result of passage of the strain through the first swine;

(b) growing the strain which is isolated in a growth medium;

(c) harvesting the cells of the strain from the growth medium;

(d) disrupting the cells of the strain by sonication for less than two minutes in an aqueous solution to obtain a mixture containing disrupted cells, capsular and sub-capsular antigens; and (e) preserving the mixture with a preservative which kills the *Actinobacillus pleuropneumoniae* to provide the vaccine.

2. The method of claim 1 wherein the harvesting is by centrifuging the growth medium and removing the cells from the growth medium.

3. The method of claim 1 wherein the aqueous solution for disrupting contains a buffer, a reducing agent to prevent a clumping of the antigenic materials, a chelating agent for metal ions and a live cell inactivating agent.

4. The method of claim 3 wherein the buffer is tris-acetate, the reducing agent is dithiothreitol, the chelating agent is ethylene diamine tetraacetic acid and the cell inactivating agent is sodium azide.

5. The method of claim 1 wherein the disrupted cells are tested to determine that all of the cells have been disrupted and that the antigenic materials are sterile.

6. The method of claim 5 wherein a cell inactivating agent as the preservative is added to the antigenic materials.

7. The method of claim 6 wherein the cell inactivating agent is sodium azide.

8. The method of claim 1 wherein the growth medium is heart infusion broth containing nicotinamide adenine dinucleotide and calcium chloride.

9. The method of claim 1 wherein the strain is grown to about a mid exponential phase of cell growth.

10. The vaccine produced by the method of claim 1.

11. The vaccine produced by the method of claim 3.

12. The vaccine produced by the method of claim 1 further comprising a hemolysin enriched supernatant.

* * * * *